United States Patent [19]

Robinson

[11] 4,047,844

[45] Sept. 13, 1977

[54] BLOOD PUMPING SYSTEM

[75] Inventor: Thomas C. Robinson, Berkeley, Calif.

[73] Assignee: Searle Cardio-Pulmonary Systems Inc., Emeryville, Calif.

[21] Appl. No.: 638,615

[22] Filed: Dec. 8, 1975

[51] Int. Cl.² .......................................... F04B 41/06
[52] U.S. Cl. ........................................ 417/3; 417/12; 417/46; 417/63; 417/339; 417/395; 251/9
[58] Field of Search ................. 417/12, 46, 138, 290, 417/316, 317, 326, 344, 346, 347, 393, 3, 339, 394, 395; 251/5, 9, 10

[56] References Cited
U.S. PATENT DOCUMENTS

| 862,867 | 8/1907 | Eggleston | 417/395 |
|---|---|---|---|
| 2,383,193 | 8/1945 | Herbert | 417/317 |
| 2,600,493 | 6/1952 | Farris | 251/5 X |
| 2,732,807 | 1/1956 | Parsegian | 417/326 |
| 3,007,416 | 11/1961 | Childs | 417/479 X |
| 3,148,624 | 9/1964 | Baldwin | 417/510 |
| 3,256,825 | 6/1966 | Limpert et al. | 417/395 |
| 3,399,693 | 9/1968 | Toma | 251/5 X |
| 3,554,672 | 1/1971 | Brandes | 417/347 |
| 3,610,782 | 10/1971 | McGuire | 417/326 |
| 3,656,873 | 4/1972 | Schiff | 417/395 |
| 3,741,687 | 6/1973 | Nystroem | 417/395 X |
| 3,811,800 | 5/1974 | Shill | 417/479 X |
| 3,938,910 | 2/1976 | Douglas | 417/12 |

Primary Examiner—William L. Freeh
Assistant Examiner—Edward Look
Attorney, Agent, or Firm—Lothrop & West

[57] ABSTRACT

A blood pumping system has a pair of integral flexible bodies each provided with an inlet and an outlet and disposed in open top cavities in a housing. The cavities have extensions holding inlet valves and outlet valves for opening and closing the inlets and outlets. A flexible diaphragm overlies the cavities and their extensions and is secured by a cover providing separate chambers over the inlet valves, the outlet valves and the bodies. Solenoid air valves are selectively energized to supply and exhaust the chambers to operate the valves and bodies. Switches responsive to the full and empty positions of the bodies govern the energization of the solenoids through control circuitry including a voltage controlled oscillator, a device for changing the frequency of the oscillator in accordance with the time of operation of at least some of the switches, and a device for ensuring at least a minimum rate of operation of the switches. Alarms are afforded after a predetermined number of switch operations have been missed.

6 Claims, 12 Drawing Figures

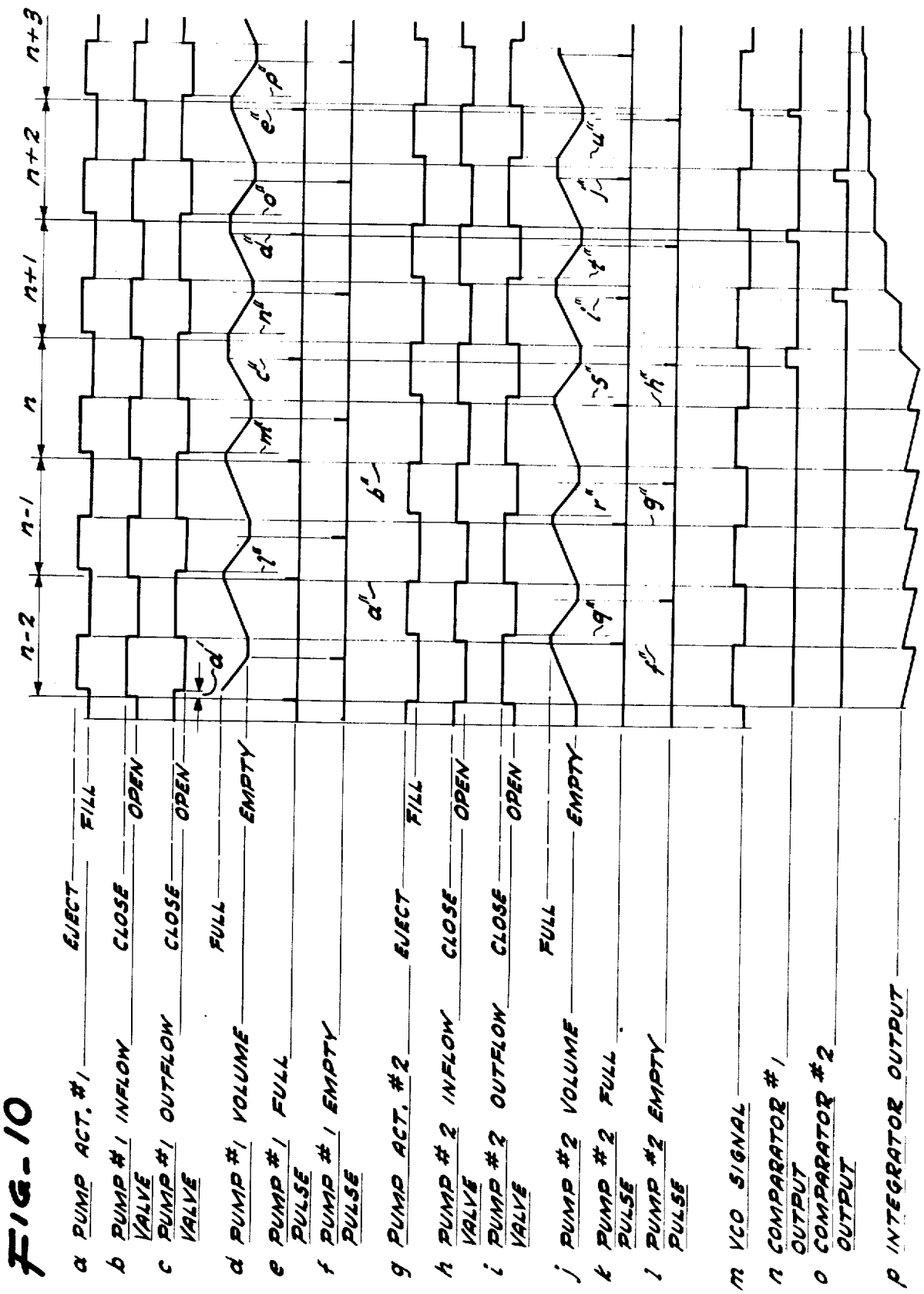

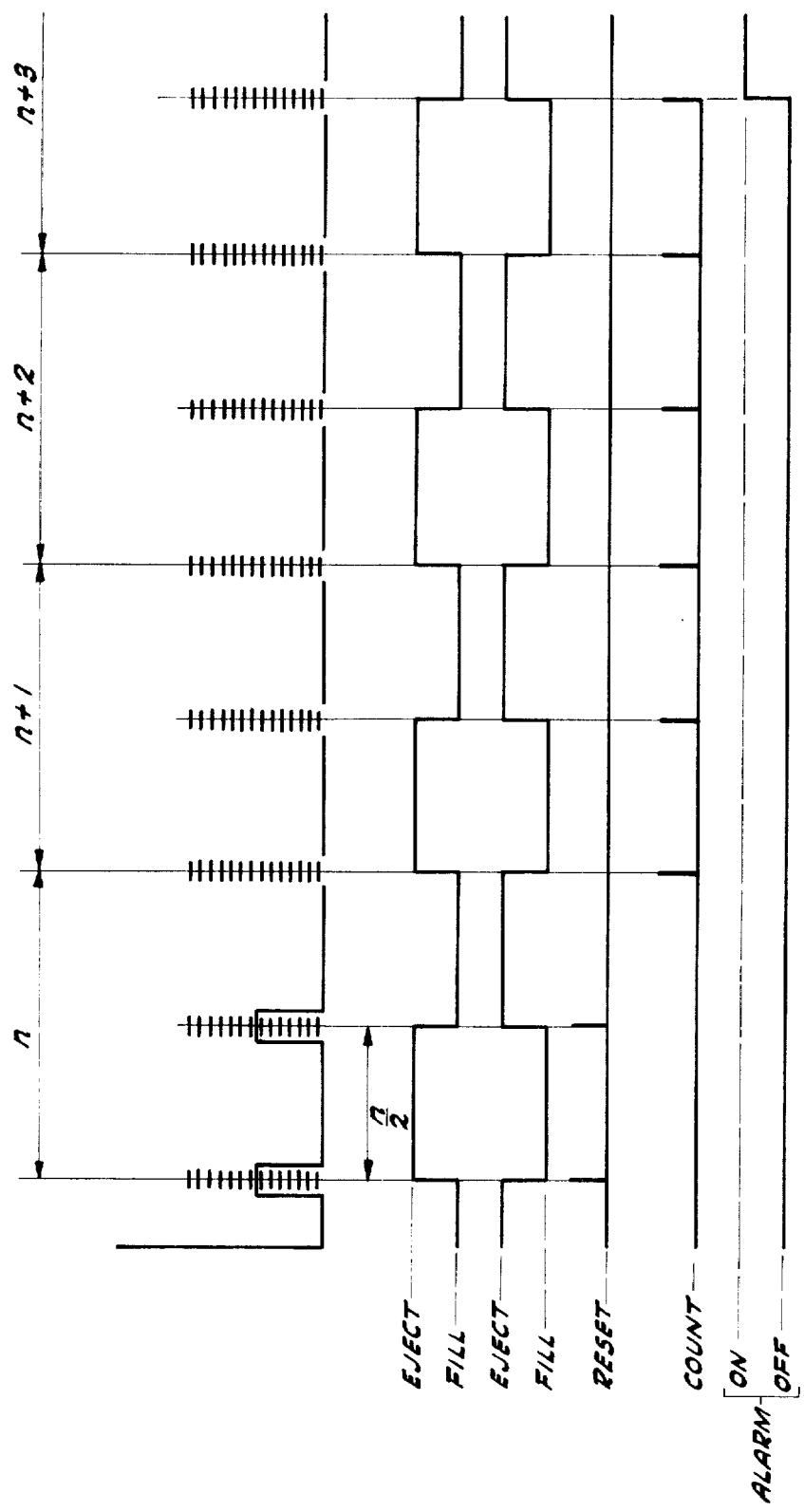

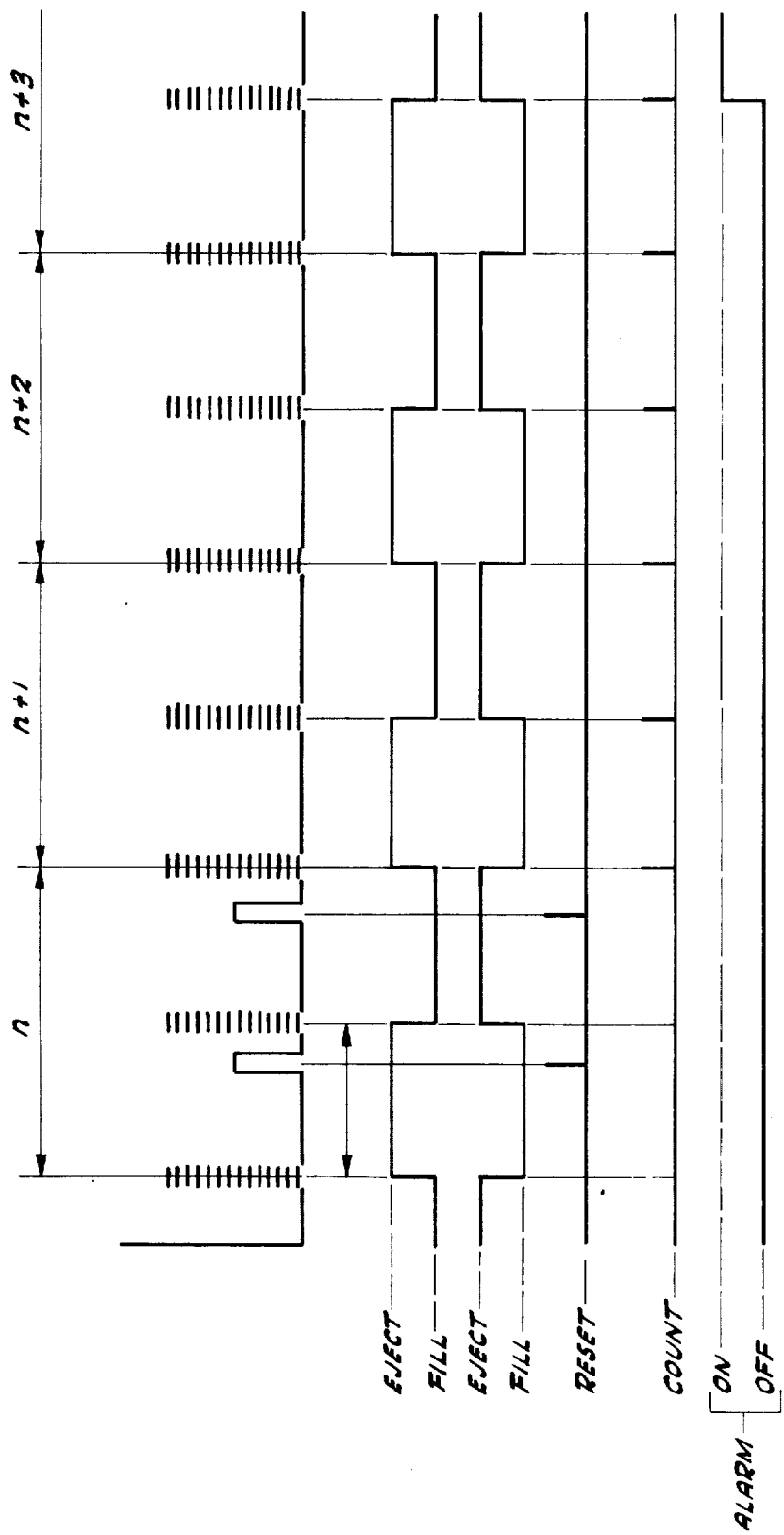

BLOOD PUMPING SYSTEM

In many environments it is necessary or desirable to augment or supplant the natural circulation of blood throughout the body by a mechanical means. While many such devices are available, there are still subsisting drawbacks connected with their use. One difficulty is the trauma to which the blood is subjected by mechanical handling, particularly in certain types of pumps. Another difficulty is the danger of air access to the blood being pumped. Another difficulty is the bulk and weight of some of the equipment, which makes it difficult to utilize in cramped environments or makes it difficult to be changed in position.

It is therefore an object of the invention to provide a blood pumping system that can be fabricated in a relatively light, portable fashion.

Another object of the invention is to provide a blood pumping system in which the former disadvantages are overcome, so that trauma to the blood is greatly reduced or virtually eliminated and access of air does not occur.

Another object of the invention is to provide an arrangement in which the rate of operation of the system is carefully and closely coordinated with a desired or natural program.

Another object of the invention is to prevent a vacuum or subatmospheric pressure on blood being taken into the pumping system by filling the pump under gravity or the patient's blood pressure or both and without suction on the blood itself or on body tissues.

Another object of the invention is to prevent excessive pressure upon the blood being forced out of the pumping system by displacing the blood by using a gas such as air under a predetermined or limited pressure acting on the blood through a flexible sheet.

A further object of the invention is to provide a generally simple, sanitary, readily maintained and long-lived structure.

Another object of the invention is to provide a blood pumping system that can readily be accommodated to various different applications and environments.

Other objects, together with the foregoing, are attained in the embodiments of the invention described in the accompanying description and illustrated in the accompanying drawings, in which:

FIG. 10 is a chart showing the time relationship of many of the events occurring during the operation of the blood pumping system;

FIG. 11 is a diagram on a time basis indicating one style of operation of the pumping system; and FIG. 12 is a diagram somewhat like FIG. 11 but showing another style of operation of the blood pumping system.

Figure 1:
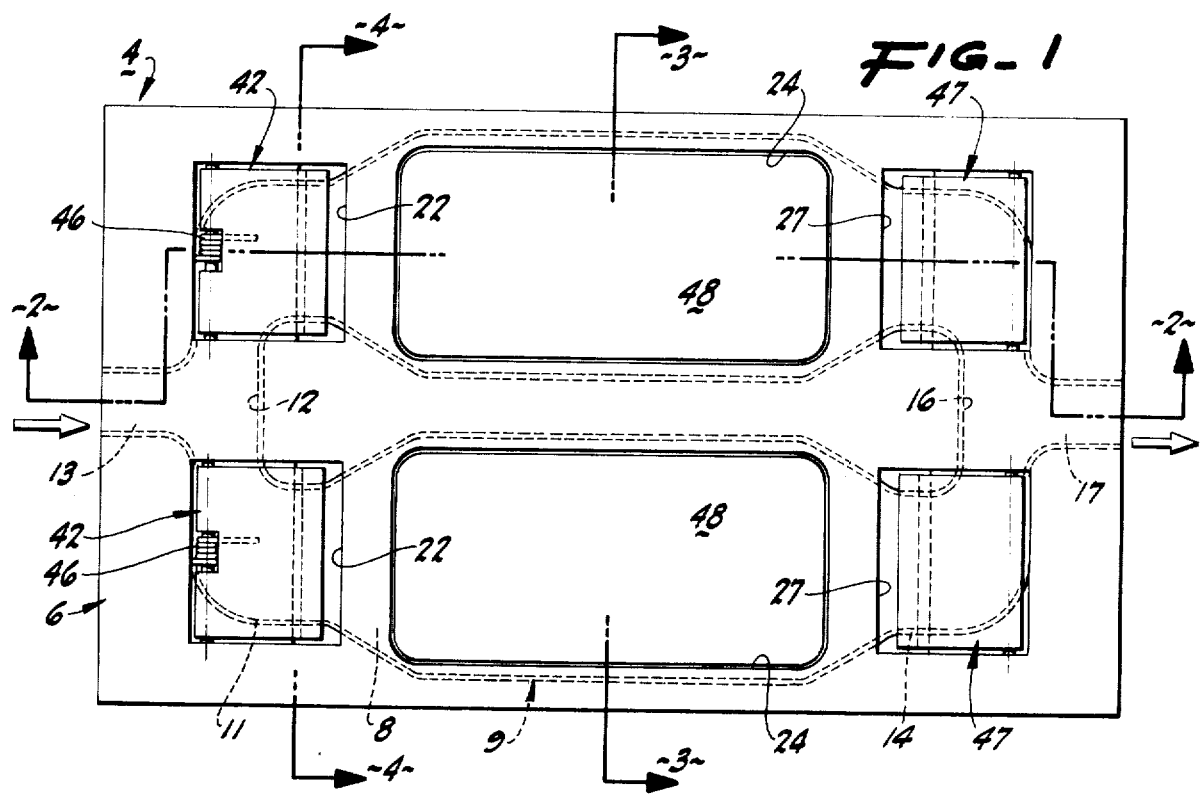
FIG. 1 is a plan, a cover and diaphragm being removed, of a blood pumping mechanism utilized in the system, the view in effect also being a cross-section on the line 1—1 of FIG. 2.

While the blood pumping system of the invention can be embodied in a large number of different ways, it has with success been embodied as disclosed herein. In this arrangement there is incorporated a pumping mechanism generally designated 4. This is a mechanical unit that takes in blood from a patient (without suction), increases the pressure on the blood and displaces and discharges the blood back to the patient. The pumping mechanism includes a pair of pumps and is symmetrical about a central plane. The pumps are substantially identical, so that the description of one applies also to the other. The pumps are arbitrarily designated #1 and #2. The pumping mechanism includes a pump block 6 including a lower plate 7 that can be disposed on any suitable support. On each side of center, the lower plate 7 is hollowed to define the lower portion of a cavity 8 having a wide and thick central portion 9, diminished to merge with an inlet valve portion 11 and enlarging into a first cross portion 12 opening to a common inlet 13. An oxygenator of any standard kind, not shown, can be connected at a convenient point in the path of blood flow and preferably is arranged to oxygenate the blood stream just in advance of the inlet 13.

At the other end, the cavity 8 has a reduced outlet valve portion 14 and a second cross portion 16 opening to a common outlet 17. A complementary upper plate 21 is similarly hollowed and additionally defines an inlet valve compartment 22 opening into the cavity. A bridge 23 separates the inlet valve compartment 22 from a central compartment 24 also open to the cavity 8, while another bridge 26 separates the central compartment from an outlet valve compartment 27.

Designed removably to occupy both cavities is a flexibly walled liner 28 or pumping envelope conveniently made of a pair of sheets of flexible material sealed around their edges except for an inlet tube 29 and an outlet tube 31 suitable for exterior connections to the patient. A sheet 32 of similar flexible material overlies the top of the upper plate 21, and a stiff cover plate 33 overlies the sheet. The plates 7 and 21, the sheet 32 and the liner 28 are positioned by removable fasteners, not shown, thus permitting ready assembly and removal and replacement of the liner and sheet.

The cover 33 above the inlet valve compartment 22 is hollowed to form an inlet valve chamber 34 provided with a port 36. Also, the cover above the central compartment 24 is formed to provide an actuator chamber 37 with a port 38. Further, the cover 33 above the outlet valve compartment 27 is shaped to provide an outlet valve chamber 29 having a port 41.

Within the inlet valve compartment of each pump is an inlet valve 42. This takes the form of a cross shaft 43 pivotally carrying one arm of a bell plate 44, the other arm of which has a rounded terminus abutting the top of the liner 28. A spring 46 around the shaft 43 urges the bell plate 44 toward the sheet 32. A similar but springless outlet valve 47 is in each outlet valve compartment 27. In the actuator compartment 24 is a plunger block 48 confined between the bridges 23 and 26 and abutting the sheet 32 and the liner 28.

Figure 2:
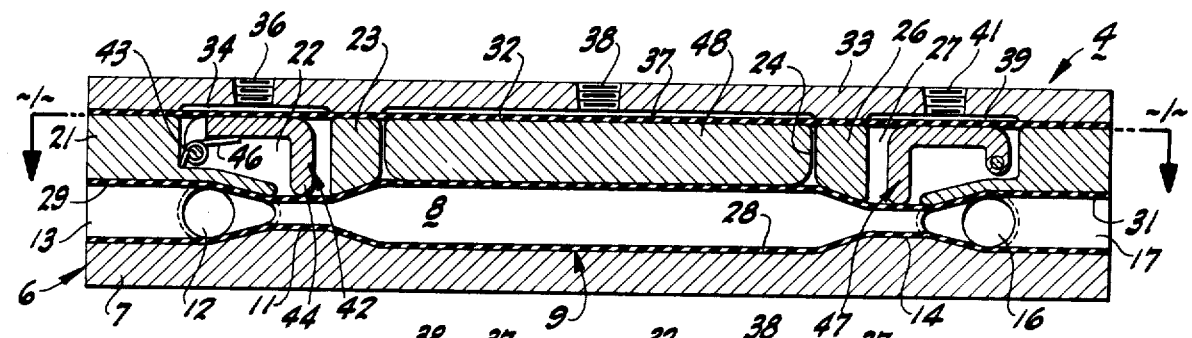
FIG. 2 is a cross-section, the planes of which are indicated by the lines 2—2 of FIG. 1.
Figure 3:
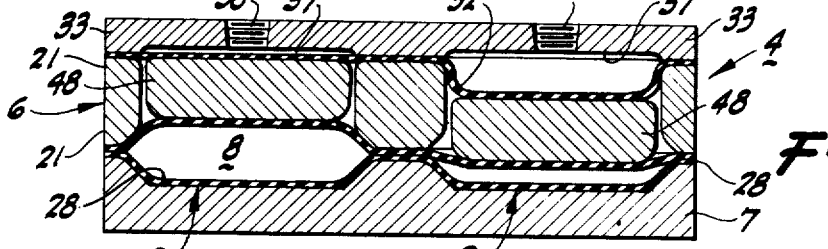
FIG. 3 is a cross-section through the device of FIG. 1, the plane of section being indicated by the line 3—3 of FIG. 1.
Figure 4:
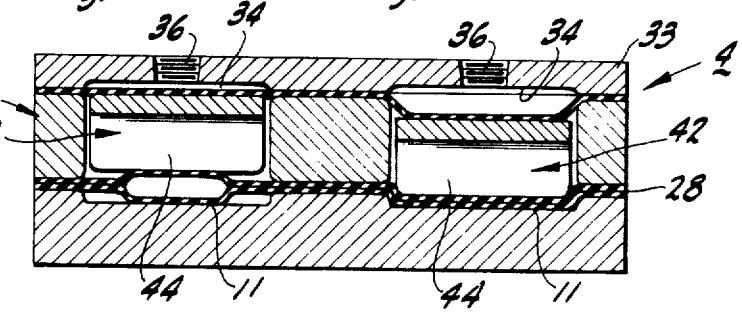
FIG. 4 is a view through the device of FIG. 1, the plane of section being indicated by the line 4—4 of FIG. 1.

In order to actuate the pumps #1 and #2, a pneumatic mechanism is preferred. For example, when the inlet valve 42 is in an upper position impelled by the spring 46, the local portion of the sheet 32 is substantially flat. When air under pressure is admitted through the port 36 into the chamber 34, the affected portion of the sheet 32 is depressed and rotates the valve bell plate 44 clockwise against the urgency of the spring. The inlet valve plate end squeezes the subjacent narrow portion of the liner or envelope 28 and precludes flow between the inlet 13 and the main or central portion 9 of that pump. In a comparable fashion, when air under pressure is admitted through the port 41 to the adjacent outlet valve chamber 39, the end of the bell plate of the outlet valve 47 is depressed and pinches off communication between the main pump portion 9 and the outlet 17. When no air under pressure is admitted through the port 38, the plunger block 48 is substantially in the upper position shown in FIG. 2, but when air under pressure is so admitted, then the local portion of the sheet 32 is deflected downwardly and displaces the plunger block 48. This forces down the upper portion of the pump envelope 28 or liner and expels a corresponding portion of the contents thereof.

With this arrangement, it is simple from time to time to disassemble the pump block 6 and to remove and resterilize or renew and replace the various flexible and working portions thereof. The valving accomplished by the rounded ends of the valve bell plates 44 is relatively gentle. Their action in compressing the inlet and outlet portions of the pump envelope produces only a small amount of blood trauma, as compared to that inflicted by a roller pump, for example.

Figure 5:
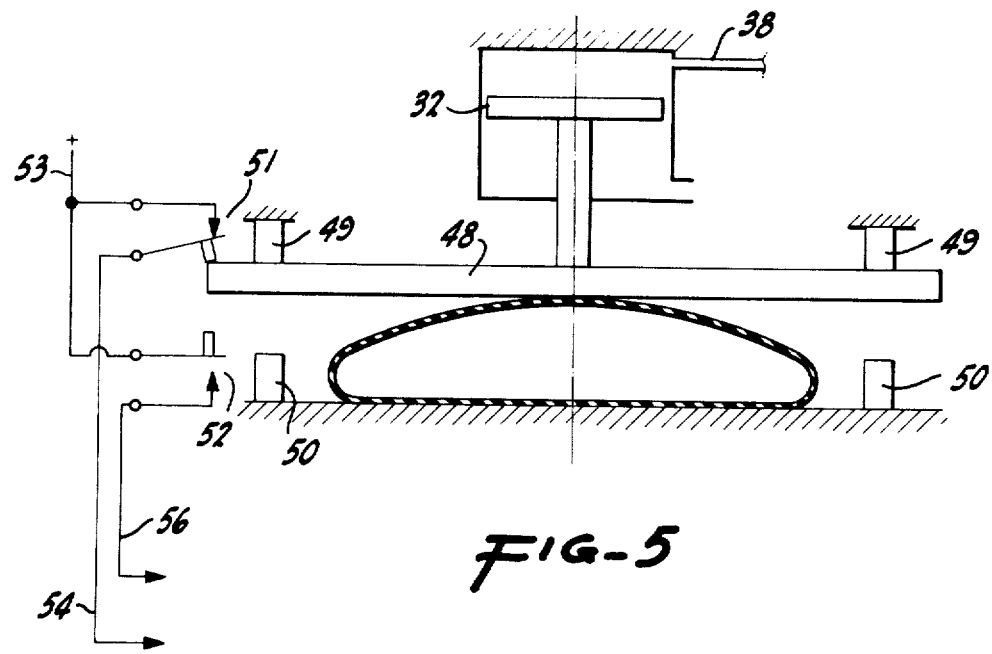
FIG. 5 is a diagrammatic showing of one of the pumping mechanisms of the sort shown in FIG. 1 with some of the ancillary equipment for control illustrated diagrammatically.
Figure 6:
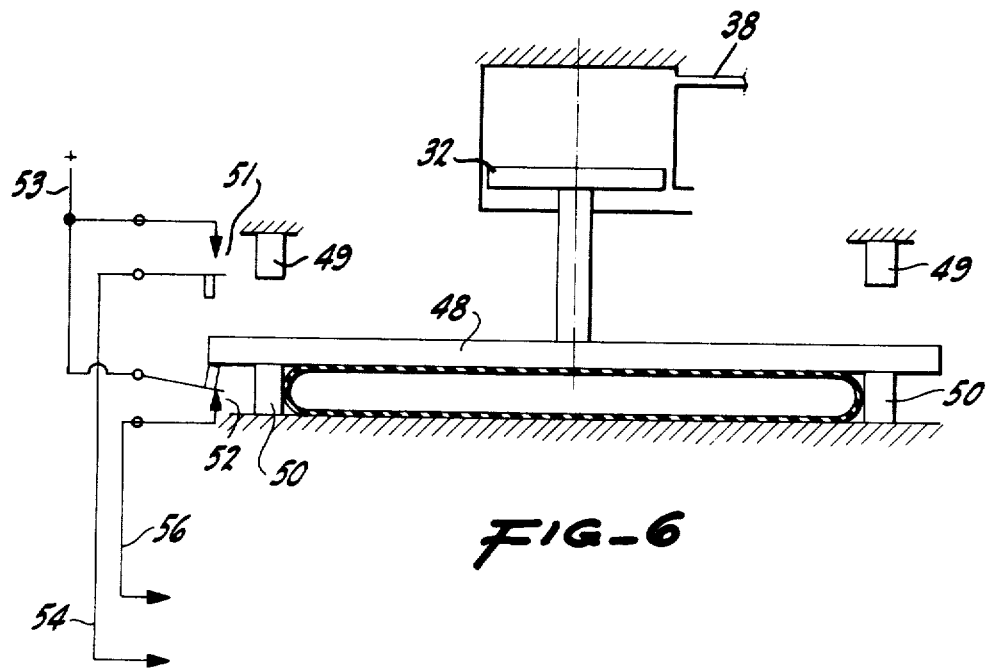
FIG. 6 is a view comparable to FIG. 5 but showing the parts in a different position.

The operation of a pumping chamber is limited in stroke, as is diagrammatically shown in FIGS. 5 and 6. When a pumping chamber is full, as shown in FIG. 5, it can be considered that the plunger block 48 is at the maximum height as set by a stop 49, the sheet 32 being represented as a piston in FIG. 5. Then, when air under pressure is let in through the port 38, the plunger block 48 is depressed until another stop 50 is encountered. The plunger block 48 thus squeezes the pump envelope 28 and deforms it to a smaller volume, expelling the corresponding contents, until the plunger block 48 abuts the lower stop 50, thus limiting the stroke to a predetermined amount. When the chamber has been substantially emptied and is in the position shown in FIG. 6, an influx of blood from the patient returns the parts to their original position against the stop 49.

The motion of the plunger block 48 or, more particularly, its extreme positions is responded to by electrical switches as part of an electrical control of the air mechanism. For each pump there is a "full" switch 51 mechanically brought into closed position just as the plunger block 48 arrives in its uppermost position, and there is an "empty" switch 52 brought into closed position just as the plunger block 48 comes into abutment with the stop 50. The switches 51 and 52 are supplied with electricity through a lead 53 from an appropriate source. The "full" switch 51 controls a circuit including a lead 54, while the "empty" switch 52 controls a circuit having a lead 56.

Figure 7:
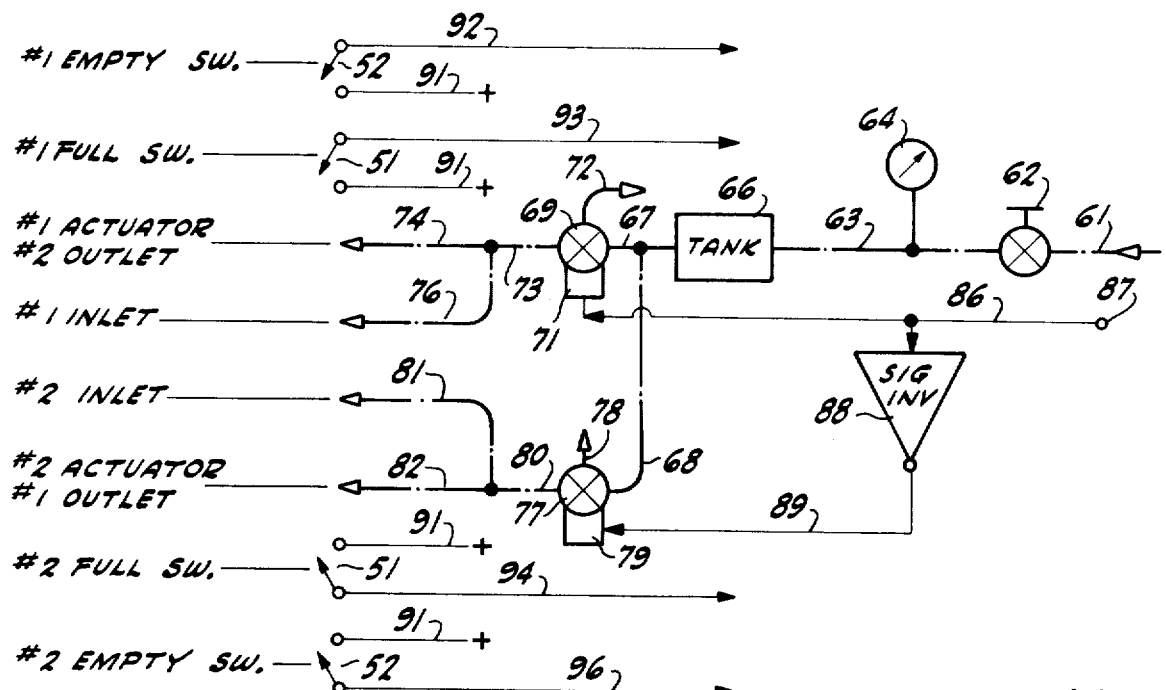
FIG. 7 is diagram of a part of the electro-pneumatic control structure for the pump.

The air flow to the valve chambers is controlled in accordance with a predetermined program by an arrangement substantially as shown in FIG. 7. Compressed air from any suitable source, not shown, is brought in through a conduit 61 and through a pressure regulating valve 62 to a pipe 63 to which a gauge 64 is connected. The pipe 63 extends into a reservoir tank 66 having a pair of outlets 67 and 68. The outlet 67 extends to an air valve 69 worked by a solenoid 71 and having a vent 72 to atmosphere. From the valve 69 a pipe 73 branches to a connection 74 to the actuator chamber port 38 of the #1 pump and to the outlet valve port 41 of the #2 pump. The pipe 73 also branches to a connection 76 to the actuator port 36 for the inlet valve of the #1 pump. In a similar way, the supply outlet 68 extends through a valve 77 having a vent 78 to atmosphere and actuated by a solenoid 79. A connection 80 from the valve 77 has two branches 81 and 82. The branch 81 extends to the actuator port 36 for the inlet valve for the #2 pump, while the branch 82 extends to the port 38 for the actuator of the #2 pump and to the port 41 for the outlet valve for the #1 pump.

The solenoid 71 is normally de-energized and is energized by current flowing in a conductor 86 having a terminal 87 connected to circuitry shown in FIG. 9 and later to be described. The conductor 86 proceeds through a signal inverter 88 having a conductor 89 extending to the solenoid 79. A signal on the conductor 86 operates both the solenoid 71 and the solenoid 79 simultaneously but with opposite effect. The two pumps #1 and #2 thus alternately fill and discharge in unison. The pump plunger blocks 48 afford feedback. As shown in Fig. 7, the empty switch 52 for the #1 pump receives current through a conductor 91 from a suitable source and sends out a corresponding signal over a conductor 92. Comparably, the full switch 51 for the #1 pump likewise receives current through the conductor 91 and sends a signal through a conductor 93. Comparably, the full switch 51 for the #2 pump receives current from the conductor 91 and sends out its own signal over a conductor 94. The empty switch 52 for the #2 pump receives current through the conductor 91 and sends a signal over a conductor 96. The effect of the signals on the conductors 92, 93, 94 and 96 is later described.

Figure 8:
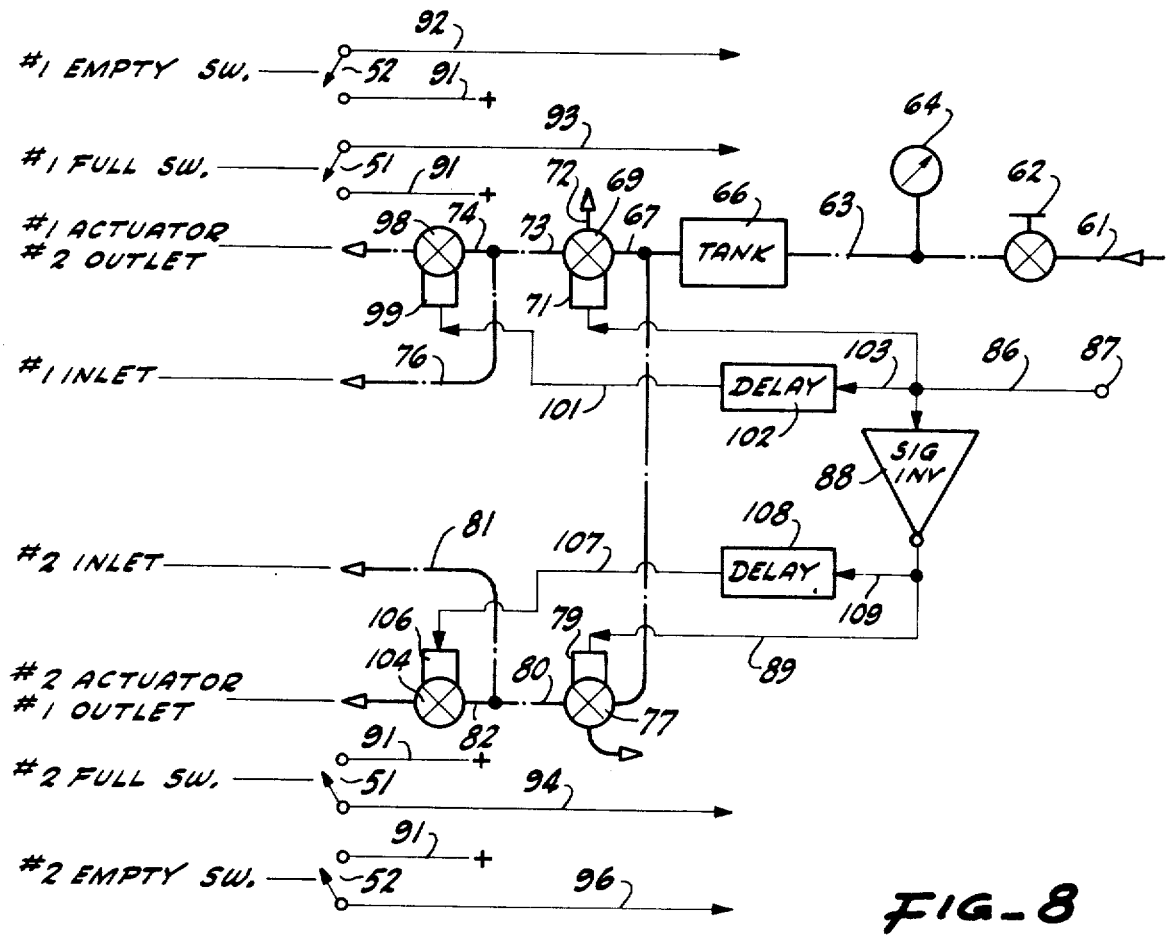
FIG. 8 is a modified version of part of the electro-pneumatic control structure shown in FIG. 7.

While the circuitry set forth in FIG. 7 is quite satisfactory under most conditions, it is sometimes desired to delay the actuation of both #1 pump and #2 pump until the inlet valves 42 are surely closed, to prevent backflow. In this instance, as shown in FIG. 8, the mechanism is exactly as shown in FIG. 7, but is augmented by the provision in the pipe connection 74 of a delay valve 98 having its own solenoid 99 connected by a conductor 101 through a delay network 102 to a lead 103 joined to the signal conductor 86. In a comparable fashion, the pipe branch 82 has a delay valve 104 actuated by a solenoid 106 joined by a conductor 107 through a delay network 108 to a lead 109 joined to the conductor 89.

In this instance, the signals in the conductor 86 are timed just as they are in connection with the FIG. 7 arrangement, and such signals are not delayed to the solenoids 71 and 79 operating the inlet valves, but are delayed in the networks 102 and 108 and cause the pump actuators and outlet valves to operate somewhat later than they otherwise would. There is thus adequate time provided for the inlet valves of the respective pumps to be fully closed before the outlet valves open and pump actuation occurs, thus making sure that there is no backflow from the pumping chambers into the inlets.

Figure 9:
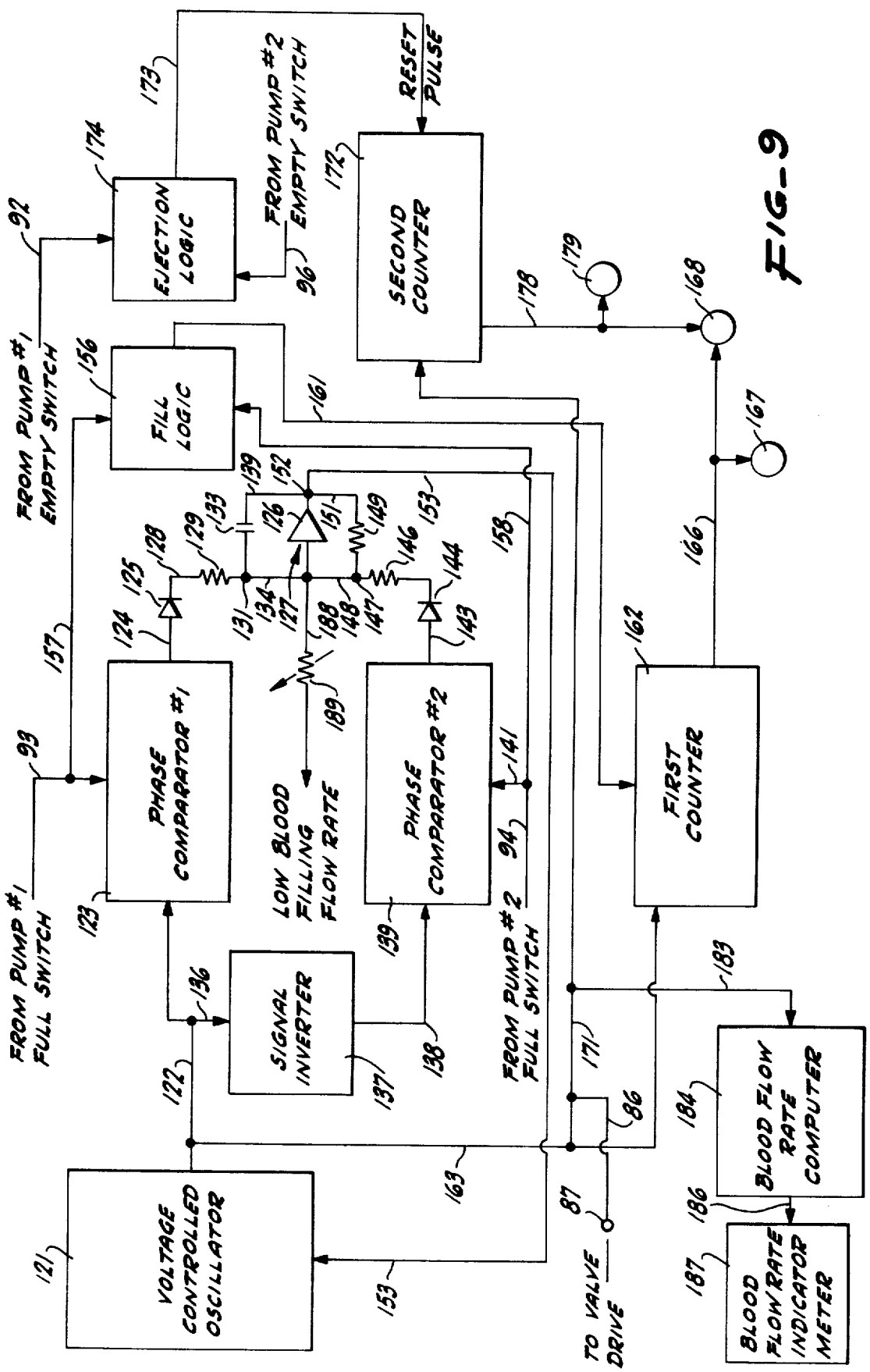
FIG. 9 is a circuit diagram indicating much of the electronic circuitry employed in the system to regulate and control the pump.

The operation of the blood pump is controlled by a system that is largely electronic and is conveniently arranged as shown in FIG. 9. A voltage controlled oscillator 121 supplies a timed signal over a conductor 122 to a #1 phase comparator 123. The phase comparator 123 also receives a signal from the #1 pump full switch 51 each time the #1 pump is full. In the #1 phase comparator 123, the pump full signal and the oscillator signal are compared with each other. A resulting signal is transmitted over a conductor 124 and through a diode 125 toward a unit 126 of an averaging integrator 127. The connection is through a conductor 128 joined through a resistor 129 to a junction 131 in a conductor 134 leading to the integrator unit 126. A capacitor 133 is connected around the unit 126.

There is a duplicate arrangement for the #2 pump. The signal from the voltage controlled oscillator 121 dispatched over the conductor 122 also goes through a conductor 136 to a signal inverter 137. From there the inverted signal travels over a conductor 138 to a #2 phase comparator 139. Also transmitted to the phase comparator 139 is a signal from the #2 pump full switch 51 travelling over conductors 94 and 141. The difference in the two pump full signals is provided as an output from the comparator 139 and travels over a conductor 143 and through a diode 144 and a resistor 146 to a junction 147. A conductor 148 from the junction 147 leads to the integrator unit 126. The junction 147 is joined through a resistor 149 and conductor 151 to the junction 152 of the integrator unit 126. The integrator 127 includes the unit 126, the capacitor 133 and the resistors 129, 146 and 149. The signals from the two phase comparators 123 and 139 are averaged in the integrator 127 and are present at the junction 152. From there a corrective voltage travels through a conductor 153 to the oscillator 121. The polarity of the corrective voltage causes the oscillator to vary its frequency in a direction to decrease the error pulse duration. This controls the rate of operation of the pump, the aim being to keep the pump operation in consonance with the supply of blood from the patient. The control also acts to effect any rate changes relatively slowly and without shock and to do so for both pumps, which are synchronized to provide a steady, smooth outflow.

The full switches 51 for both the #1 pump and the #2 pump are also effective on a fill logic unit 156. The #1 pump full switch 51 is connected thereto by a conductor 157, while the #2 pump full switch 51 is connected thereto by a conductor 158. Corresponding signals from the fill logic unit 156 are carried by a conductor 161 to a first counter 162. This counter also receives signals from the voltage controlled oscillator 121 over a conductor 163. Normally the first counter 162 receives a signal from the voltage controlled oscillator that is immediately cancelled by a signal from the fill logic 156 that the pump has filled. If the #1 pump does not fill, then the resulting absence of reset or cancel signal from the fill logic 156 permits the first counter 162 to accumulate oscillator 121 signals to a predetermined extent; for example, six counts. The last accumulated signal is dispatched from the first counter 162 over a conductor 166 to a visual alarm 167 and also to an audible alarm 168 to energize them. This alerts an attendant that for some reason, such as an unfilled pump, the fill logic has not been actuated and that attention is needed. Whenever the fill logic 156 is subsequently actuated, any accumulation in the first counter 162 is cancelled and the alarms 167 and 168 are not actuated or, if already actuated, are discontinued.

A similar arrangement is provided in case the pumps do not empty completely. The conductor 163 from the oscillator 121 has a branch conductor 171 extending to a second counter 172. A conductor 173 joins the second counter to an ejection or empty logic unit 174 receiving a signal from the #1 pump empty switch 52 through the conductor 92. An empty signal from the #2 pump empty switch 52 is carried by the conductor 96. Whenever a signal is received from the voltage controlled oscillator 121 in the second counter 172, that signal is normally reset or cancelled by a signal on the conductor 173 from the ejection logic. If, however, the pump empty switches 52 of either the #1 pump of the #2 pump, or both, fail to deliver signals to the ejection logic 174, then no corresponding cancel or reset pulse is available. As soon as the second counter 172 accumulates the incoming pulses to a sufficient extent; say, six such pulses, then the second counter 172 sends a signal over a conductor 178 to actuate a visual alarm 179 and also to actuate the audible alarm 168.

Additionally, the signals from the voltage controlled oscillator 121 are utilized to afford an indication of the operation of the pumping system. Branched from the conductor 171 is a conductor 183 leading to a blood flow rate computer 184. This affords any appropriate manipulation on any program base desired. The computer ouput is carried through an extension 186 to a blood flow rate meter 187. By inspection, the user can get an indication of the instantaneous blood flow rate.

The pump frequency is not permitted to go below a set or chosen value. Joined to the integrator 127 by a conductor 188 is a control, such as a settable resistor 189. This, with the integrator circuitry, establishes the minimum value of the control voltage from the integrator 127 to the oscillator 121 and so puts a lower limit on pump frequency.

The conductor 86 (FIGS. 7 and 8) in FIG. 9 extends between the conductor 171 and the terminal 87 and carries the voltage controlled oscillator 121 signals to the terminal 87 (FIG. 7 and FIG. 8), so that signals from the oscillator 121 are supplied to the conductor 86 for timing the pump actuator and valve operations, as described.

The general operation of the mechanism is diagrammatically illustrated in FIG. 10. Various events are shown as ordinates and various time base cycles are shown as abscissae. There is a datum cycle $n$ and two cycles in a series preceding the datum cycle, designated $n-1$ and $n-2$. There are also several subsequent cycles in the series, designated $n+1$, $n+2$ and $n+3$.

Line $a$ shows the condition of the #1 pump actuator, there being a succession of ejection events and filling events of approximately equal duration, except for a slight delay $d'$ in eject actuation.

Line $b$ indicates the position of the #1 pump inlet or inflow valve as being either open or closed, those events occupying substantially equal time.

Line $c$ indicates the position of the #1 pump outlet or outflow valve, either open or closed, corresponding generally to the #1 pump actuation, the delay $d'$ being in effect.

Line $d$ shows the instantaneous volume of the #1 pump, ranging between full and empty.

Line $e$ shows the timing of the signals or pulses from the #1 pump when full. Comparably, line $f$ shows pulses from the #1 pump when empty.

Line $g$ shows the operations of filling and ejecting by the actuator for the #2 pump. This is comparable to line

*a* for the #1 pump and shows a similar actuation delay time.

Line *h* indicates the position of the #2 pump inlet or inflow valve, either closed or open.

Line *i* indicates the position of the oulet or outflow valve of the #2 pump as open or closed.

Line *j* shows the instantaneous volume of the #2 pump, just as is shown in line *d* for the #1 pump.

Line *k* shows the occurrence of the full pulses from the #2 pump and can be compared with line *e*.

Line *l* shows the #2 pump empty pulses, comparable to line *f*.

Line *m* indicates the occurrence of pulses or signals from the voltage controlled oscillator 121.

Line *n'* affords an indication of the output from the #1 comparator 123 not only as to its presence or absence, but particularly as to its variable duration.

Line *o* similarly shows the presence or absence of an output signal from the #2 comparator 139 as to presence or absence and particularly as to variable duration.

Line *p* affords an indication of the output of the integrator 127.

It will be noted that the volume of the pump chambers increases to the points *a"* to *j"*, remains constant between those points and the respective related points *l"* to *u"*, and then decreases followed by an empty plateau and then repeats the increase.

In the operation of the device, the low blood filling rate is set by the variable resistor 189 (FIG. 9) to establish a minimum rate of operation of the pump. Ordinarily, the supply of blood from the patient to both of the pumps is considerably in excess of the amount required to meet the minimum setting, so both pumps normally fill more rapidly than the minimum requires. The minimum setting is adjustable and may be set high enough to establish a steady state of the system, and may even be so high that the pumps do not expand completely on intake. Each pump when full supplies from its full switch 51 a signal to its respective phase comparator. For example, the #1 pump periodically energizes the comparator 123 supplying a signal to the integrator 127. Comparably, the #2 pump when full has its full switch 51 closed to supply a similar signal through the conductor 141 to the comparator 139, itself supplying a signal to the integrator 127.

In the integrator, the full signals from the two pumps are averaged and generate an outgoing, error correcting pulse through the conductor 153. This pulse has a voltage polarity tending to correct the frequency of the oscillator 121, so that the pumps are retained in step, as illustrated in FIG. 10 by the cycles $n-2$ and $n-1$, indicating that the system is in stable equilibrium.

Assume that for some reason during the last half of cycle *n* the #1 pump fills prematurely and so sends out an early full pulse, such as *c* as indicated by the shortened time interval in line *e*, FIG. 10. The early signal then affects the phase comparator and the integrator to produce an error signal as indicated in line *n* for the #1 comparator. This changes the voltage output from the integrator 127, after averaging with a similar error signal, line *o*, in the output of comparator #2 due to similar early filling of the #2 pump. As shown in FIG. 10, the change in voltage affects the oscillator 121 to reduce the duration of the error signal and to bring the frequency of operation of the pumping structure back into equilibrium with the rate or amount of blood supplied to the pumps. As will be observed in FIG. 10, the error signals occur with diminished duration in the latter portions of cycles $n+1$ and $n+2$, and the system has gotten back into normal step during cycle $n+3$ and thereafter.

Since the amount of blood pumped is in proportion to the freqency of operation of the two pumps, since their normal volume is fixed, the number of the signals from the voltage controlled oscillator, whatever its adjusted or controlled rate, is effective on the blood flow rate computer 184 to actuate the indicator meter 187 to afford a visual display of the instantaneous rate of blood pumping.

Should it occur that the supply of blood to the pumps for any reason decreases to an amount so that the fill period is very slow and extends for more than one-half of a voltage controlled oscillator period, such as *n*, then when such oscillator pulse occurs, the pump has not yet completely filled. There is thus no fill output signal, such as indicated by the line *e* or the line *k*, and as also indicated in FIG. 11. Since the pump full signals are not generated, there are no signals to the fill logic unit 156 and no output therefrom through the conductor 161 to reset the first counter 162. The successive signals from the oscillator 121 through the conductor 163 therefore are accumulated in the first counter 162 for a predetermined number of signals.

Particularly as shown in FIG. 11, there are no resetting fill signals at the end of cycle *n*, so that a count begins at the end of cycle *n*. This is repeated in the middle of cycle $n+1$ and at the end of that cycle, is repeated again in cycle, $n+2$ and at the end of that cycle, and when it occurs again in the middle of cycle $n+3$, the accumulation of six uncancelled oscillator signals is effective through the conductor 166 to energize the visual alarm 167 and the audible alarm 168, thereby advising an attendant that the pumps are not filling. Under these conditions, the pumps maintain a minimum frequency. The diodes 126 and 144 block reverse current flow into the comparators 123 and 139, and the integrator then integrates to a voltage controlled by the adjustable low filling rate as set by the variable resistor 189 and the ratio of the resistor 149 to the resistor 189. The oscillator 121 then puts out pulses at a minimum rate.

In a somewhat similar fashion, as particularly indicated in FIG. 12, it may occur that when one filling pump chamber becomes full, the other, emptying pump chamber may not have entirely completed its emptying function and may not have afforded any pump empty signal. In that event, there is no input to the ejection logic unit 174 from the #1 pump empty switch, for there is no signal carried by the conductor 92, nor from the #2 pump empty switch carried by the conductor 96. Consequently, there is no reset signal output through the conductor 173 to the second counter 172. Sine each pulse of the oscillator 121 is supplied to the second counter through the conductor 171, the counter 172 accumulates a predetermined number of the incoming pulses. For example, there are reset pulses due to complete emptying as shown in FIG. 12 in the first and second halves of cycle *n*. Those signals provide reset pulses, as illustrated, for the second counter. When the pump empty signals no longer cause any reset, the oscillator pulses are accumulated as illustrated in pulses $n+1$ and $n+2$ until in the middle of pulse $n+3$ there is a sufficient accumulation of counts to cause the second counter 172 to put out a signal over the conductor 178 to actuate the visual alarm 179 and to energize the common audible alarm 168. Whenever the pumping system departs from an equilibrium condition, either by failing to fill completely or by failing to empty completely, the attendant is immediately notified. The system restores itself to equilibrium by a subsequent full signal and an empty signal. These energize the fill logic 156 and the ejection logic 174 to put out reset signals over the conductors 161 and 173 and restore the counters 162 and 172 to normal, nonaccumulative use. Should the blood flow from the patient to the pump suddenly decrease, then the output of the integrator 127 correspondingly decreases with time until a lower, stable flow rate is established.

What is claimed is:

1. A blood pumping system comprising a pair of pumps each having a pumping chamber defined by a flexible enclosure expandable to a full condition and compressible to an empty condition;

means defining blood inlets to both said chambers;
    means defining blood outlets from both said chambers;
    inlet valves for controlling flow through said inlets;
    outlet valves for controlling flow through said outlets;
    first actuators for said inlet valves;
    second actuators for said outlet valves;
    third actuators movable in one direction for compressing said enclosures to said empty condition and movable in the reverse direction to permit said enclosures to expand to full condition;
    electric controllers for said first, second and third actuators;
    means responsive to movement of said third actuator to its extreme positions to provide position signals;
    means for regulating the rate of operation of said controllers including a variable oscillator supplying a sequence of timed signals to repeatedly and sequentially open said inlet valves, close said outlet valves and permit said pumping chamber to expand to full condition then close said inlet valves, open said outlet valves and move said third actuators in said one direction;
    a signal comparator;
    means for supplying said oscillator signals to said comparator;
    means for supplying said position signal to said comparator; and
    means controlled by said comparator in response to differences in the time of receipt of said position signals and said oscillator signals for varying the frequency of said oscillator.

2. A blood pumping system as defined in claim 1 in which said flexible enclosures, said inlet defining means and said outlet forming means are comprised of an integral, flexible, hollow body.

3. A system as defined in claim 1 wherein said means responsive to movement of said third actuator are electric switches.

4. A system as defined in claim 1 wherein said means controlled by said comparator varies the frequency of said oscillator in a direction to decrease the output from said comparator.

5. A system as defined in claim 1 including means providing a count of the signals from said oscillator and means responsive to each position signal for cancelling said count.

6. A system as defined in claim 5 including means for accumulating said counts and means responsive to accumulation of a predetermined number of counts by said accumulating means for actuating an alarm device.

* * * * *